US012667359B2

(12) United States Patent
Kulak et al.

(10) Patent No.: US 12,667,359 B2
(45) Date of Patent: Jun. 30, 2026

(54) EXPANDABLE DEVICES FOR TREATING BODY LUMENS

(71) Applicant: Covidien LP, Mansfield, MA (US)

(72) Inventors: Julie Kulak, Costa Mesa, CA (US);
Khoa Dang Vu, Santa Ana, CA (US);
Ramon Carrillo, Santa Ana, CA (US)

(73) Assignee: Covidien LP, Mansfield, MA (US)

( * ) Notice: Subject to any disclaimer, the term of this patent is extended or adjusted under 35 U.S.C. 154(b) by 284 days.

(21) Appl. No.: 18/063,223

(22) Filed: Dec. 8, 2022

(65) Prior Publication Data

US 2023/0225735 A1    Jul. 20, 2023

Related U.S. Application Data

(60) Provisional application No. 63/287,984, filed on Dec. 10, 2021.

(51) Int. Cl.
*A61B 17/12* (2006.01)

(52) U.S. Cl.
CPC ... *A61B 17/12022* (2013.01); *A61B 17/12113* (2013.01); *A61B 17/12168* (2013.01)

(58) Field of Classification Search
CPC ........ A61B 17/12022; A61B 17/12168; A61B 17/12113
See application file for complete search history.

(56) References Cited

U.S. PATENT DOCUMENTS

| | | | | |
|---|---|---|---|---|
| 2017/0224355 A1* | 8/2017 | Bowman | ............ | A61B 17/1214 |
| 2019/0223878 A1* | 7/2019 | Lorenzo | ........... | A61B 17/12031 |
| 2020/0367897 A1* | 11/2020 | Wolfe | .............. | A61B 17/00234 |
| 2021/0212698 A1* | 7/2021 | Connor | ........... | A61B 17/12172 |

* cited by examiner

*Primary Examiner* — Darwin P Erezo
*Assistant Examiner* — Christina C Lauer
(74) *Attorney, Agent, or Firm* — Fortem IP LLP

(57) ABSTRACT

Devices, systems, and methods for treating vascular defects are disclosed herein. One aspect of the present technology, for example, includes an occlusive device comprising a mesh having a low-profile state for intravascular delivery to the aneurysm and a deployed state. The mesh may comprise a tubular mesh configured to curve along its longitudinal dimension when implanted in an aneurysm cavity.

18 Claims, 10 Drawing Sheets

EXPANDABLE DEVICES FOR TREATING BODY LUMENS

CROSS-REFERENCE TO RELATED APPLICATION(S)

The present application claims the benefit of priority to U.S. Patent Application No. 63/287,984, filed Dec. 10, 2021, which is incorporated by reference herein in its entirety.

TECHNICAL FIELD

The present technology relates to expandable devices for treating body lumens. Particular embodiments are directed to intrasaccular occlusive devices for treating aneurysms.

BACKGROUND

Intracranial saccular aneurysms occur in 1% to 2% of the general population and account for approximately 80% to 85% of non-traumatic subarachnoid hemorrhages. Recent studies show a case fatality rate of 8.3% to 66.7% in patients with subarachnoid hemorrhage. Endovascular treatment of intracranial aneurysms emerged in the 1990s with the advent of the Guglielmi detachable coil system (Boston Scientific, Natick, MA), which includes packing the aneurysm sac with metal coils to reduce or disrupt the flow of blood into the aneurysm, thereby enabling a local thrombus or clot to form which fills and ultimately closes off the aneurysm. The use of coil embolization to treat aneurysms substantially increased after the publication of favorable clinical data, including evidence that disability or death at the 1-year follow-up occurred in 30.9% of patients treated surgically but only 23.5% in patients treated with coil embolization.[4] Similarly, these trials showed the overall morbidity and mortality at 1 year was 12.6% for surgical clipping and 9.8% for endovascular coiling (amongst patients with no prior history of subarachnoid hemorrhage).

Although coiling has proven to have better outcomes than surgical clipping for both ruptured and unruptured aneurysms, treating complex aneurysms using conventional coiling is challenging. This is especially true for wide-necked aneurysms. Coil segments may protrude from the aneurysm sac through the neck of the aneurysm and into the parent vessel, causing serious complications for the patient. To address this, some treatments include temporarily positioning a balloon within the parent vessel across the neck of the aneurysm to prevent the coils from migrating across the neck during delivery. Alternatively, some treatments include permanently positioning a neck-bridging stent within the parent vessel across the neck of the aneurysm to prevent the coils from migrating across the neck during delivery. While balloon-assisted or stent-assisted coiling for wide-neck aneurysms has shown better occlusion rates and lower recurrence than coiling alone, the recanalization rate of treated large/giant aneurysms can be as high as 18.2%. Moreover, the addition of a balloon or stent and its associated delivery system to the procedure increases the time, cost, and complexity of treatment. Deployment of the stent or balloon during the procedure also greatly increases the risk of an intraprocedural clot forming, and can damage the endothelial lining of the vessel wall. Permanently positioning a stent within the parent vessel increases the chronic risk of clot formation on the stent itself and associated ischemic complications, and thus necessitates the use of dual anti-platelet therapy ("DAPT"). DAPT, in turn, increases the risk and severity of hemorrhagic complications in patients with acutely ruptured aneurysms or other hemorrhagic risks. Thus, neck-bridging stents are not indicated for the treatment of ruptured aneurysms.

The above-noted drawbacks associated with balloon- and stent-assisted coiling techniques influenced the development of intraluminal flow diverting stents, or stent-like structures implanted in the parent vessel across the neck of the aneurysm that redirect blood flow away from the aneurysm, thereby promoting aneurysm thrombosis. Flow diverters have been successfully used for treating wide-neck, giant, fusiform, and blister-like aneurysms. However, because they are positioned in the parent vessel, flow diverters require DAPT to avoid clot formation on the stent itself and ischemic complications. This, in turn, increases the risk and severity of hemorrhagic complications in patients with acutely ruptured aneurysms or other hemorrhagic risks. Thus, flow diverters are not indicated for the treatment of ruptured aneurysms. Flow diverters have also shown limited efficacy in treating bifurcation aneurysms (35-50%).

Endosaccular flow disrupting devices have been gaining momentum over the last decade, generally driven by their potential to provide the intra-aneurysmal flow disruption of coiling with the definitive remodeling at the aneurysm—parent vessel interface achieved by intraluminal flow diverters. Currently existing endosaccular devices are typically mesh devices configured to be deployed completely within the aneurysm sac, with the interstices of the mesh covering the aneurysm neck and reconstructing the aneurysm—parent vessel interface. The implant disrupts the blood flow entering and exiting the aneurysm sac (resulting in stasis and thrombosis) and supports neoendothelial overgrowth without requiring DAPT (unlike endoluminal flow diverters). Thus, endosaccular devices can be used to treat wide-necked aneurysms and ruptured aneurysms. Moreover, because the device is placed completely within the aneurysm sac, the parent and branch vessels are unimpeded and can be accessed for any further retreatment or subsequent deployment of adjunctive devices during treatment.

Accordingly, there is a need for improved devices and methods for treating aneurysms.

SUMMARY

The present technology is directed generally to devices, systems, and methods for the treatment of vascular defects, and in particular, to endosaccular occlusive devices for treating ruptured and un-ruptured intracranial wide-neck, bifurcation, and sidewall aneurysms. The occlusive device may comprise an expandable tubular mesh. The subject technology is illustrated, for example, according to various aspects described below, including with reference to FIGS. 1-8. Various examples of aspects of the subject technology are described as numbered clauses (1, 2, 3, etc.) for convenience. These are provided as examples and do not limit the subject technology.

Several embodiments of the present technology comprise an occlusive device for treating an aneurysm. The occlusive device can comprise an expandable tubular member defining a lumen therethrough. The tubular member can have a first open end region, a second open end region, an intermediate portion between the first and second open end regions, and a longitudinal axis extending between the first and second end regions. The tubular member can have a low-profile state for intravascular delivery to the aneurysm and an expanded state in which the tubular member has a preset bend along the longitudinal axis such that, when the tubular member is implanted within an aneurysm cavity in an expanded state, the tubular member curves around a portion of the dome of the aneurysm such that the first and second end regions are spaced apart from one another. According to some embodiments, the tubular member is a mesh. For example, the tubular member can be a tubular braid formed of a plurality of interwoven filaments or a stent formed of a laser cut tube or laser cut sheet that has been rolled into tubular form.

According to several embodiments, the tubular member has a substantially constant diameter along its length. In particular embodiments, the tubular member has a varying diameter along its length. In some embodiments, the tubular member has a partial toroidal shape.

In some embodiments, the occlusive device comprises an expandable tubular mesh structure defining a lumen therethrough. The tubular mesh can have a first closed end region, a second closed end region, and a longitudinal axis extending between the first and second end regions. The tubular mesh has a low-profile state for intravascular delivery to the aneurysm and an expanded state in which the tubular mesh has a preset bend along the longitudinal axis such that, when the tubular member is implanted within an aneurysm cavity in an expanded state, the tubular member curves around a portion of the dome of the aneurysm, thereby forming an open toroid.

Several aspects of the present technology include an occlusive device for treating an aneurysm, the device comprising an expandable mesh formed of a plurality of filaments and defining an interior volume, wherein the mesh has a low-profile state for intravascular delivery to the aneurysm and an expanded state in which the mesh forms a toroid.

According to some embodiments, a device for treating an aneurysm comprises a mesh have a globular shape in an expanded configuration, wherein the mesh is configured to be implanted in an aneurysm in the expanded configuration. The mesh can comprise a proximal end region, a distal end region, and a longitudinal axis extending therebetween. The mesh can comprise an outer shell, an inner shell wholly contained by the outer shell, and a column extending along the longitudinal axis of the mesh. In some embodiments, the distal end region of the mesh forms a curved surface that is concave towards an interior region of the mesh. According to several embodiments, the outer shell and the inner shell are continuous with one another at the distal end region of the mesh. The distal end region of the mesh can form a curved surface and an opening along the curved surface. In some embodiments, the distal end region does not include a hub. In some embodiments, the column extends through an interior region of the inner shell. In other embodiments, the column terminates distally at an opening at a proximal end region of the inner shell. The outer shell can be ball-shaped and/or the inner shell can be ball-shaped. The outer shell and the inner shell can have the same or different shapes and sizes. In some embodiments, the mesh is a braid.

BRIEF DESCRIPTION OF THE DRAWINGS

Many aspects of the present disclosure can be better understood with reference to the following drawings. The components in the drawings are not necessarily to scale. Instead, emphasis is placed on illustrating clearly the principles of the present disclosure.

DETAILED DESCRIPTION

The present technology may comprise, for example, an occlusive device configured to be placed within an aneurysm (e.g., a cerebral aneurysm), as opposed to an intravascularly placed stent, which eliminates the need for dual anti-platelet treatment and which lowers procedural complications. According to several embodiments of the present technology, the occlusive device comprises an expandable tubular mesh member defining a lumen therethrough. The tubular member may have a first closed end region, a second closed end region, and a longitudinal axis extending between the first and second end regions. In some embodiments, the tubular member has a low-profile state for intravascular delivery to the aneurysm and an expanded state in which the tubular member has a preset bend along the longitudinal axis such that, when the tubular member is implanted within an aneurysm cavity in an expanded state, the tubular member curves around a portion of the dome of the aneurysm and forms an open toroid.

Figure 1:
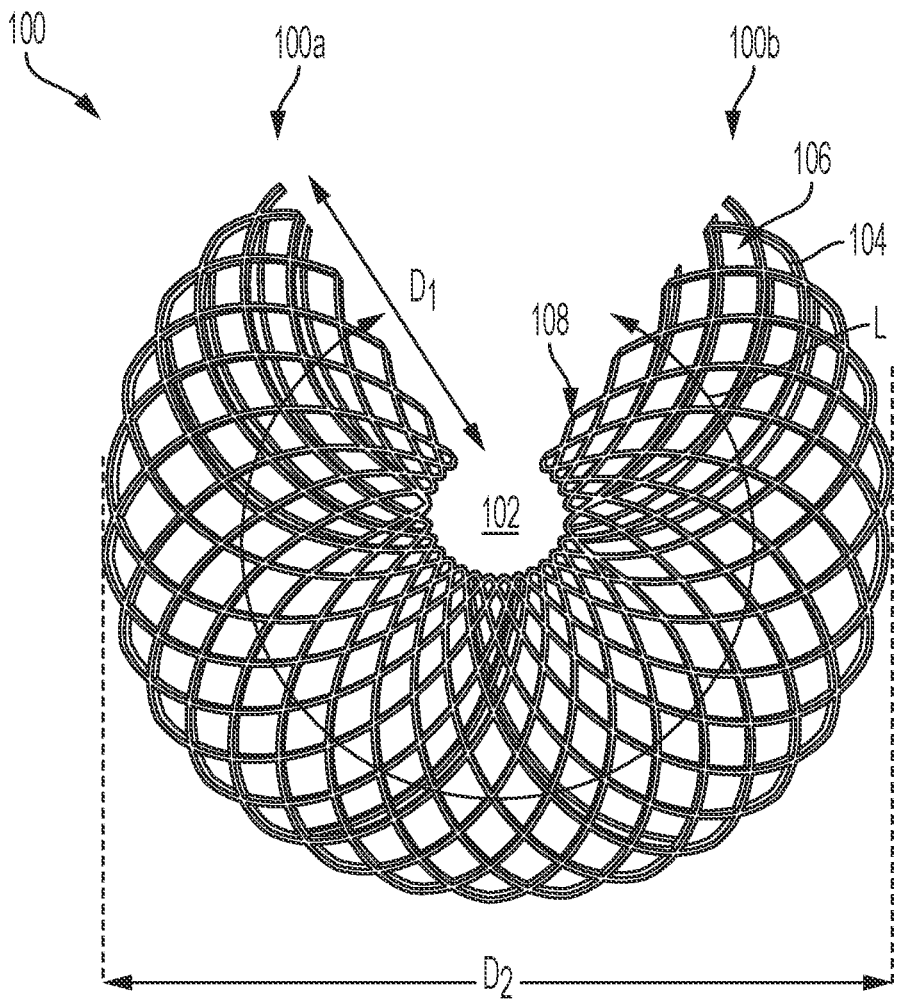
FIG. 1 is a side view of an occlusive device configured in accordance with several embodiments of the present technology.

FIG. 1 is a side view of an occlusive device 100 (or "device 100") configured in accordance with several embodiments of the present technology. The occlusive device 100 may comprise a flexible tubular structure configured to be implanted within an aneurysm, such as a cerebral aneurysm. The tubular structure can comprise a mesh 104 having a first end region 100a, a second end region 100b, and an intermediate region extending between the first and second end regions 100a, 100b along a longitudinal dimension L of the mesh 104. The mesh 104 may comprise a plurality of interconnected members defining a plurality of pores 106 therebetween. The mesh 104 can have a first opening at the first end region 100a and a second opening 100b at the second end region 100b.

Figure 4A:
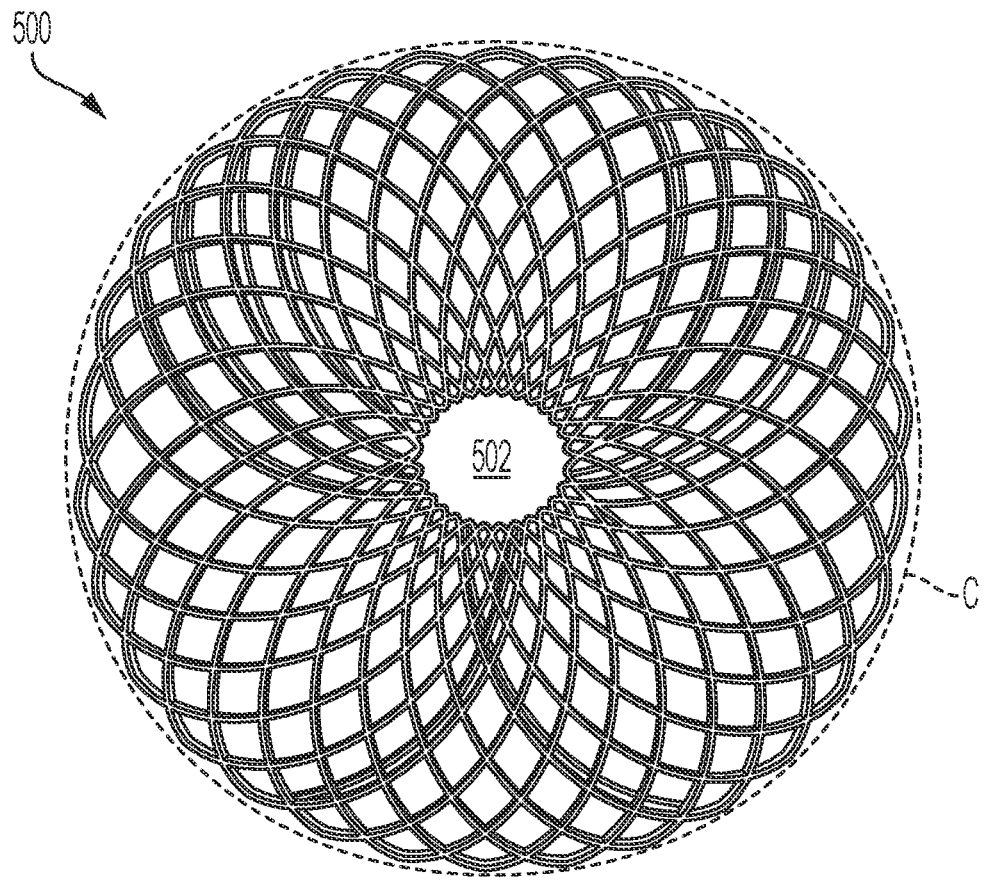
FIGS. 4A-4C illustrate occlusive devices having different shapes in accordance with several embodiments of the present technology.

The device 100 has a low-profile state (not shown) for intravascular delivery to the aneurysm and a deployed state in which the device 100 is configured to be positioned within the interior cavity of the aneurysm. As shown in FIG. 1, in a deployed state, the mesh 104 can be biased to curve about its longitudinal dimension L such that it at least partially surrounds a central opening 102. The mesh 104 can form a partial toroid (as shown in FIG. 1) or a full toroid (as shown in FIG. 4A). The mesh 104 can have a substantially constant diameter along its longitudinal dimension, or can have a varying diameter along its longitudinal dimension.

Figure 2A:
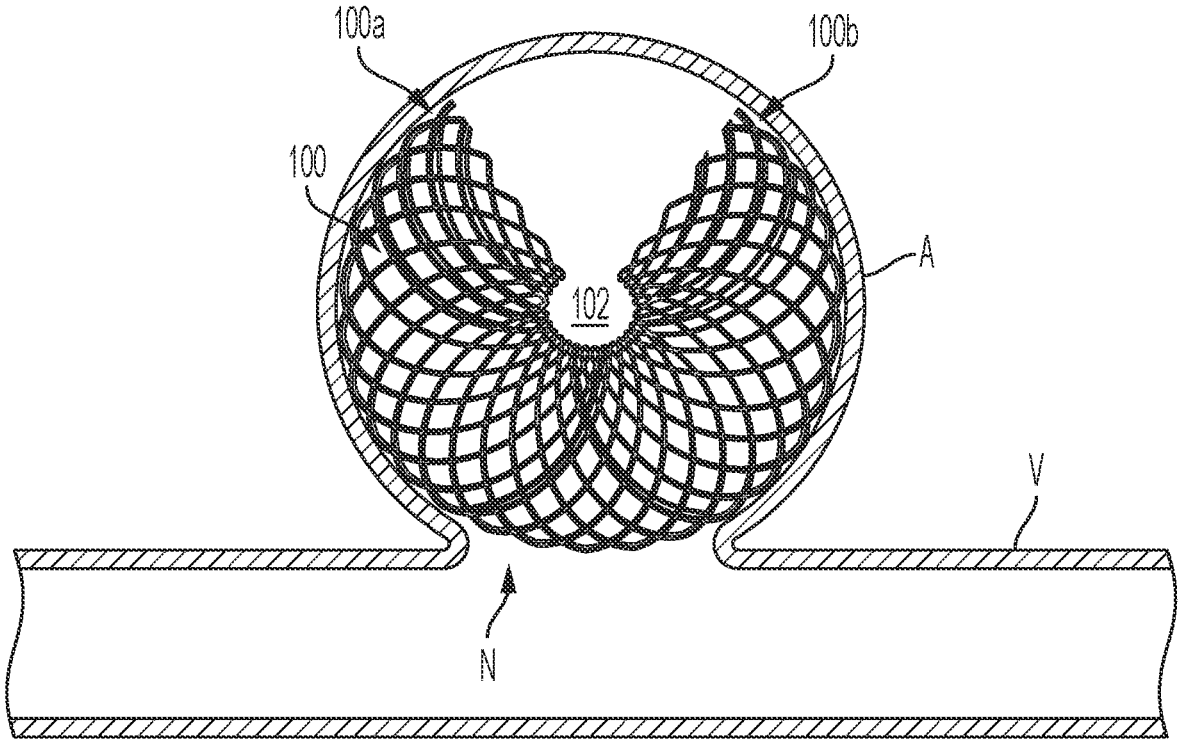
FIGS. 2A and 2B show the occlusive device of FIG. 1 positioned within an aneurysm in accordance with several embodiments of the present technology.
Figure 2B:
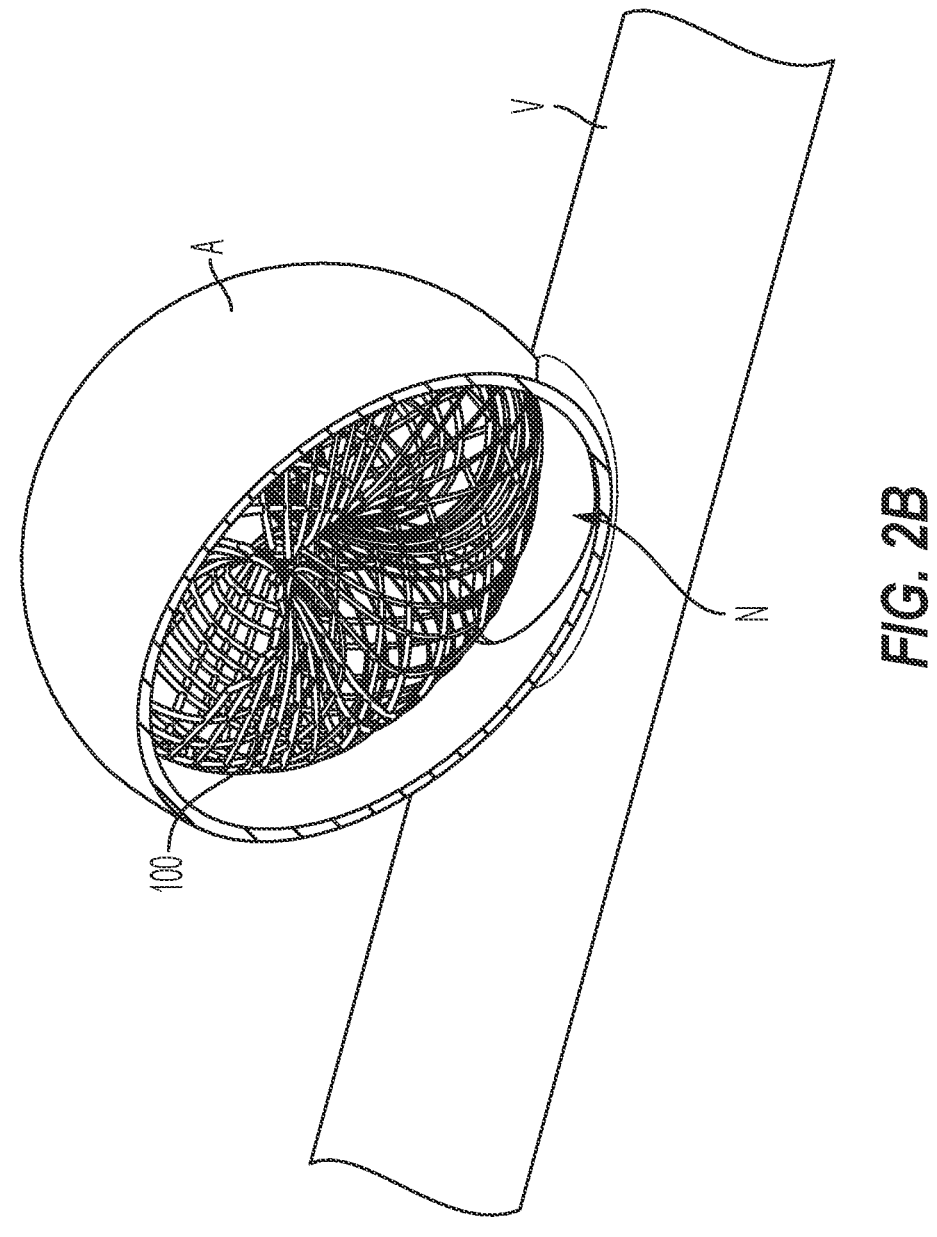

FIGS. 2A and 2B are different views of the device 100 positioned within an aneurysm. As shown, when the tubular structure is implanted within an aneurysm cavity in an expanded state, the tubular structure curves around a portion of the dome of the aneurysm such that the first and second end regions 100a, 100b are spaced apart from one another. When the device 100 is implanted, at least a portion of the tubular structure is positioned over the neck N of the aneurysm, thereby reducing blood flow entering the sac of the aneurysm and providing a scaffolding that promotes endothelialization across the covered portion of the neck, thus further reducing inflow.

According to some embodiments, the mesh 104 is a stent formed of a laser cut tube or a laser cut sheet that has been rolled into tubular form. In other embodiments, the mesh 104 is a tubular braid formed of a plurality of interwoven filaments. For example, the tubular structure may be formed of a plurality of wires, at least some of which (e.g., 25% of the wires, 50% of the wires, 80% of the wires, 100% of the wires, etc.) are made of one or more shape memory and/or superelastic materials. Some or all of the wires may have a diameter between about 0.0010 inches and about 0.0012 inches, about 0.0010 inches, about 0.0011 inches, 0.0012 inches (at least prior to etching). In some embodiments, some or all of the wires may be drawn-filled tubes ("DFT") having a radiopaque core (e.g., platinum) surrounded by a shape memory alloy and/or superelastic alloy (e.g., Nitinol, cobalt chromium, etc.).

All or a portion of the length of the tubular structure may have one or more coatings or surface treatments. For example, some or all of the tubular structure may have a lubricious coating or treatment that reduces the delivery force of the device 100 as the device 100 is advanced through the delivery catheter. In some embodiments, the coating may be relatively hydrophilic, such as a phosphorocholine compound. Additionally or alternatively, some or all of the tubular structure (or components thereof) may have a coating or treatment (the same as the lubricious coating, or a different coating) that enhances blood compatibility and reduces the thrombogenic surface activity of the braid (e.g., an antithrombogenic coating). In these and other embodiments, at least a portion of the tubular structure can be made of other suitable materials.

In any of the foregoing embodiments, auxiliary fibrous materials may be optionally to the tubular structure by weaving, tying, or other suitable permanent attachment methods.

Figure 3:
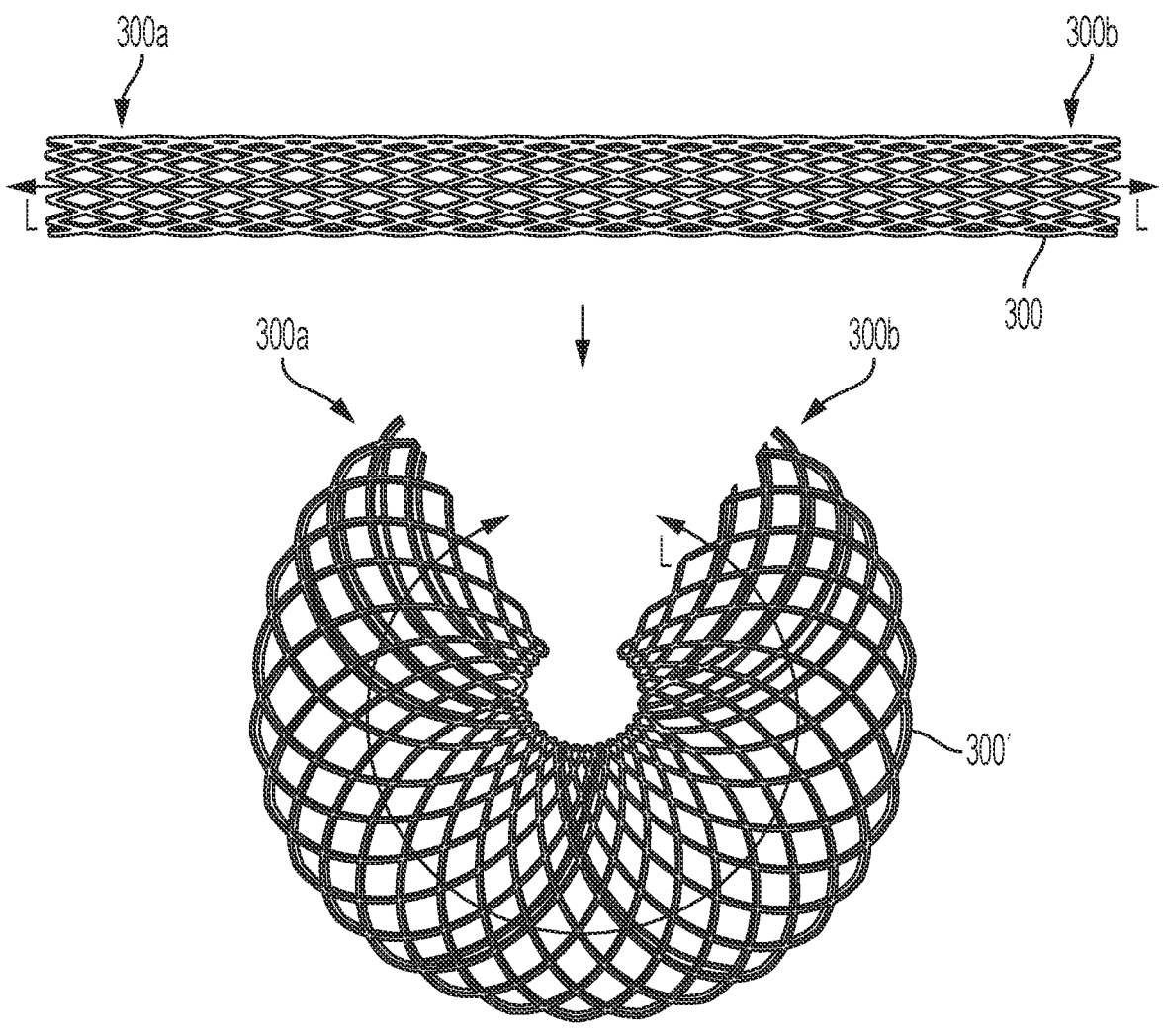
FIG. 3 illustrates a method of forming an occlusive device of the present technology.

FIG. 3 depicts a method of forming an occlusive device 300. The occlusive device 300 can be similar to the device 100. As shown, the tubular structure can be bent or curved into a partial toroidal shape and heat set while held in that configuration so that the tubular structure remains biased towards the heat set shape when unconstrained.

According to some embodiments, an embolic material, may be delivered into the interior volume of the tubular structure. The embolic material may be delivered through the same catheter that delivered the tubular structure, or through a different catheter that has been advanced to the aneurysm A such that a distal portion is positioned within the structure. When the physician has been satisfied that the aneurysm is sufficiently occluded, with or without the additional embolic material, the device 100 may be detached from the delivery member (such as a pusher member) via one or more detachment mechanisms.

In some cases, the physician may choose to deliver additional coils or embolic material (such as a liquid embolic) to the aneurysm to facilitate delivery, engagement with the aneurysm, or increase of the packing density or fill volume. In these scenarios, the physician may withdraw the pusher member from the delivery catheter and, while maintaining the tip of the delivery catheter within the aneurysm sac (beyond the mesh positioned across the neck), the physician may push the additional embolic material through the delivery catheter and into the aneurysm. The embolic material may comprise one or more liquid embolics, polymers, hydrogels, foams, framing components, and other suitable embolic elements. Any of these embodiments can increase the packing density or fill volume to avoid recanalization of the aneurysm.

Some or all of the tubular structure may comprise a radiopaque material. The methods of the present technology may be performed under fluoroscopy such that the radiopaque portions of the device 100 may be visualized by the physician to ensure proper neck coverage.

All or a portion of the tubular structure can comprise a resilient mesh material such as, without limitation, nickel titanium (nitinol or otherwise known as NiTi), stainless steel, polymers, cobalt chromium, and/or combinations thereof. Exemplary known biomedical polymeric families include, without limitation, polymers such as polyphosphazenes, polyanhydrides, polyacetals, poly(ortho esters), polyphosphoesters, polycaprolactones, polyurethanes, polylactides, polycarbonates, polyamides, and/or a combination thereof.

In one exemplary embodiment, the resilient mesh material is formed of woven strands of polymer material, such as, without limitation, nylon, polypropylene or polyester. The polymer strands can be filled with a radiopaque material which allows the physician treating the aneurysm to fluoroscopically visualize the location of the device within the vasculature. Radiopaque filler materials preferably include bismuth trioxide, tungsten, titanium dioxide or barium sulfate, or radiopaque dyes such as iodine. The resilient mesh material can be formed by strands of radiopaque material.

In some embodiments, the strands of the resilient mesh material are formed using both metal and polymer braided strands. Combining the metal strands with the polymer strands into a braid changes the flexibility characteristics of mesh. The force required to deploy and/or collapse such a mesh portion is significantly reduced over that required for a mesh portion that includes only metal mesh strands. However, the radiopaque characteristics of the mesh for fluoroscopic visualization are retained. Metal strands forming such a device includes, without limitation, stainless steel, gold, platinum, platinum/iridium, nitinol, and/or combinations thereof. Polymer strands forming the device can include nylon, polypropylene, polyester, Teflon®, and/or combinations thereof. Further, polymer strands of the mesh material can be chemically modified to make them radiopaque with known techniques such as, without limitation, by using gold deposition onto the polymer strands, or by using ion beam plasma deposition of suitable metal ions onto the polymer strands. The resilient mesh material can also be formed with filaments or strands of varying diameter and/or varying flexibility. By varying the size or flexibility of the polymer strands, the flexibility characteristics of the mesh, upon deployment, can also be varied. By varying the flexibility characteristics, both the deployed and collapsed configuration of the 14 resilient mesh body can be varied or changed to substantially any desired shape.

Not only can the mesh be formed of both polymer strands or filaments and metal strands or filaments, but it can be formed using filaments of different polymer materials. For example, different polymer materials having different flexibility characteristics can be used in forming the mesh. This alters the flexibility characteristics to change the resultant configuration of the mesh body in both the deployed and the collapsed positions. Such biomedical polymers are readily known and available in the art and can be derived from polymeric families such as, without limitation, polyphosphazenes, polyanhydrides, polyacetals, poly (ortho esters), polyphosphoesters, polycaprolactones, polyurethanes, polylactides, polycarbonates, polyamides, and/or a combination thereof.

FIG. 4A is a side view of an occlusive device 500 (or "device 500") configured in accordance with several embodiments of the present technology. The device 500 may comprise a flexible tubular structure configured to be implanted within an aneurysm, such as a cerebral aneurysm. The tubular structure can comprise a mesh formed of a plurality of interconnected members defining a plurality of pores therebetween.

The device 500 has a low-profile state (not shown) for intravascular delivery to the aneurysm and a deployed state in which the device 500 is configured to be positioned within the interior cavity of the aneurysm. As shown in FIG. 4A, in a deployed state, the mesh can be biased to curve about its longitudinal dimension such that it completely surrounds a central opening 502 (i.e., a donut shape). As such, the mesh does not have any open longitudinal ends. The mesh can have a substantially constant diameter along its longitudinal dimension, or can have a varying diameter along its longitudinal dimension.

According to some embodiments, the mesh is a stent formed of a laser cut tube or a laser cut sheet that has been rolled into tubular form. In other embodiments, the mesh is a tubular braid formed of a plurality of interwoven filaments, for example as detailed above.

Figure 4B:
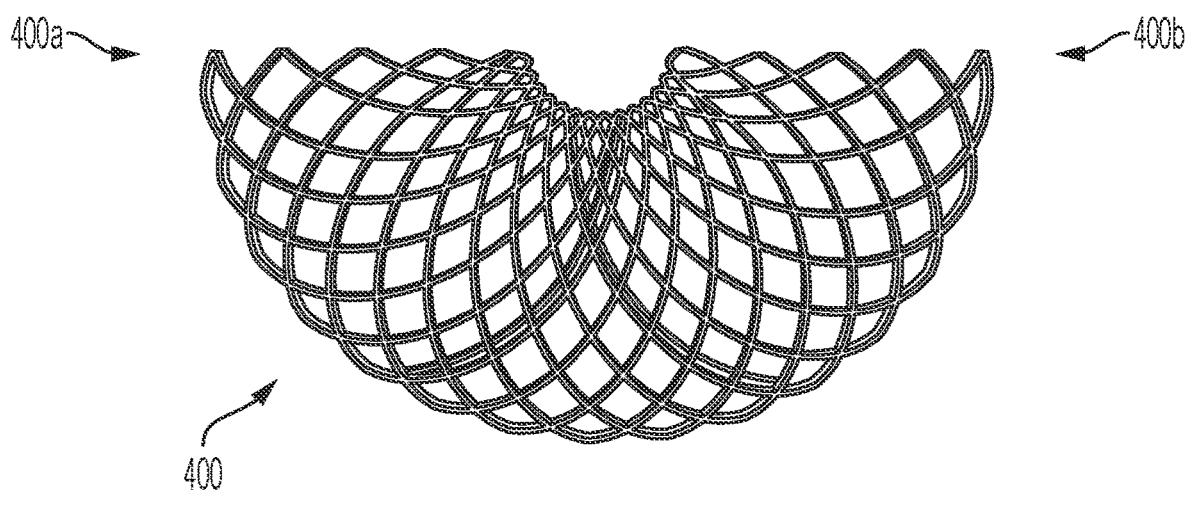

FIG. 4B is a side view of an occlusive device 400 (or "device 400") configured in accordance with several embodiments of the present technology. The device 400 may comprise a flexible tubular structure configured to be implanted within an aneurysm, such as a cerebral aneurysm. The tubular structure can comprise a mesh having a first end region 400a, a second end region 400b, and an intermediate region extending between the first and second end regions 400a, 400b along a longitudinal dimension L of the mesh. The mesh 104 may comprise a plurality of interconnected members defining a plurality of pores therebetween. The mesh can have a first opening at the first end region 400a and a second opening 400b at the second end region 400b.

Figure 4C:
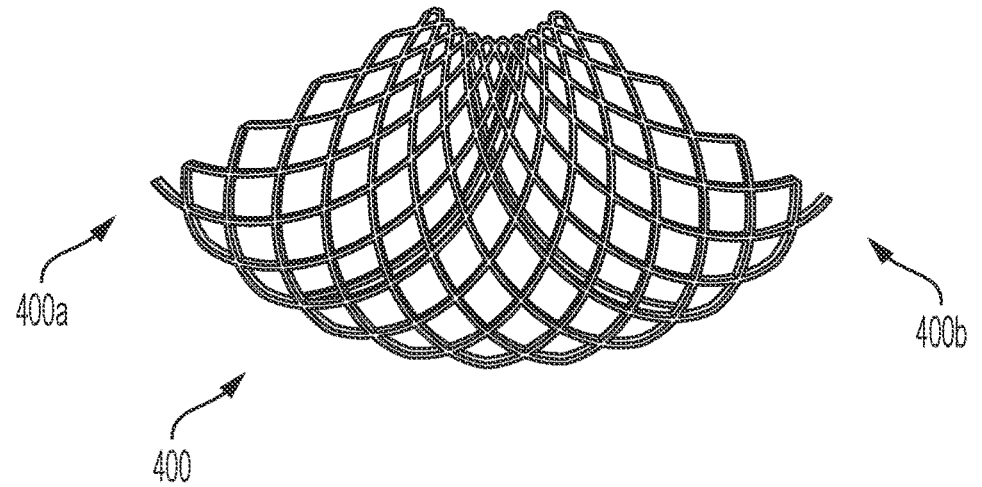

The device 400 has a low-profile state (not shown) for intravascular delivery to the aneurysm and a deployed state in which the device 400 is configured to be positioned within the interior cavity of the aneurysm. As shown in FIG. 4B, in a deployed state, the mesh can be biased to curve about its longitudinal dimension L such that it extends around no more than 180 degrees of a circle (i.e., a half-donut). In some embodiments, the mesh is sized such that it extends between 90 degrees and 180 degrees of a circle (as shown in FIG. 4C). The mesh can have a substantially constant diameter along its longitudinal dimension, or can have a varying diameter along its longitudinal dimension.

According to some embodiments, the mesh is a stent formed of a laser cut tube or a laser cut sheet that has been rolled into tubular form. In other embodiments, the mesh is a tubular braid formed of a plurality of interwoven filaments, for example as detailed above.

Figure 5:
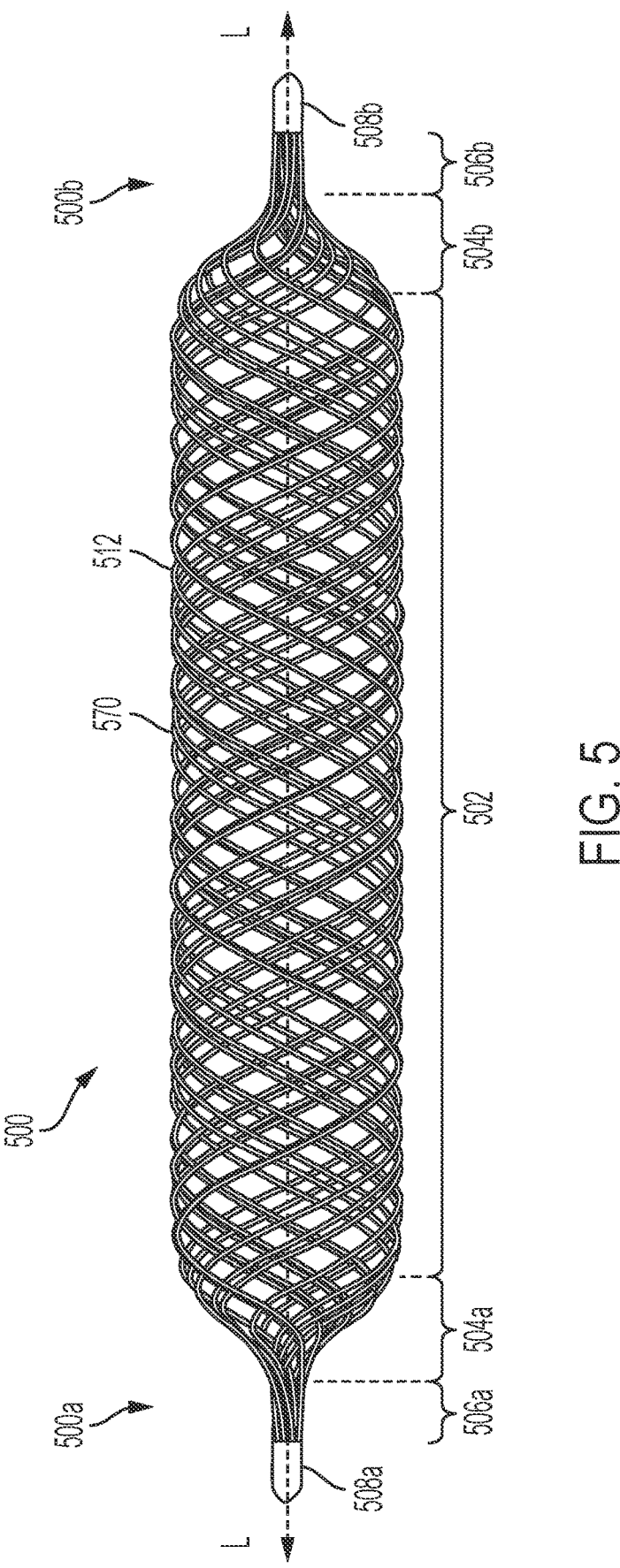
FIG. 5 is a side view of an occlusive device configured in accordance with several embodiments of the present technology.
Figure 6:
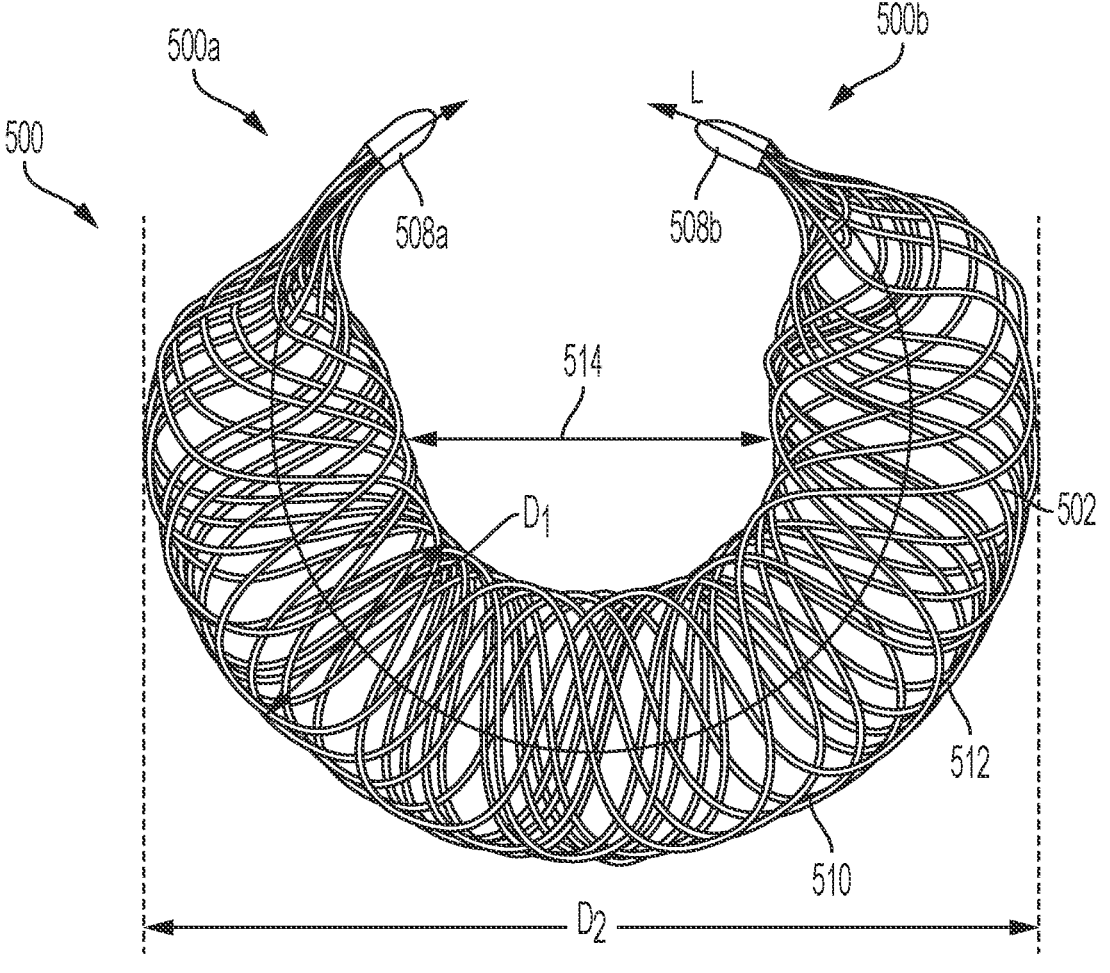
FIG. 6 is a side view of the occlusive device shown in FIG. 5 in a bent configuration.

FIGS. 5 and 6 show an occlusive device 500 (or "device 500") configured in accordance with several embodiments of the present technology. The occlusive device 500 may comprise a flexible cylindrical structure configured to be implanted within an aneurysm, such as a cerebral aneurysm.

The tubular structure can comprise a mesh 512 having a first end region 500a, a second end region 500b, and an intermediate region 502 extending between the first and second end regions 500a, 500b along a longitudinal dimension L of the mesh 512. The mesh 512 may comprise a plurality of interconnected members defining a plurality of pores therebetween. The mesh 512 can be closed at both the first and second end regions 500a, 500b. The sidewall of the mesh 512 defines an interior region.

The first and second longitudinal ends of the mesh 512 can be held together by first and second connectors 508a, 508b. The first end region 500a can comprise the first connector 508a, a narrowed portion 506a, and a tapered portion 504a. The narrowed portion 506a extends between the first connector 508a and the tapered portion 504a, and the tapered portion 504a extends between the narrowed portion 506a and the intermediate region 502. The second end region 500b can comprise the second connector 508b, a narrowed portion 506b, and a tapered portion 504b. The narrowed portion 506b extends between the second connector 508b and the tapered portion 504b, and the tapered portion 504b extends between the narrowed portion 506b and the intermediate region 502.

The device 500 has a low-profile state (not shown) for intravascular delivery to the aneurysm and a deployed state in which the device 500 is configured to be positioned within the interior cavity of the aneurysm. As shown in FIG. 6, in a deployed state, the mesh 512 can be biased to curve about its longitudinal dimension L such that it at least partially surrounds a central opening defined by a distance 514 between opposing sidewalls of the mesh 512. The mesh 104 can have a substantially constant diameter along its longitudinal dimension, or can have a varying diameter along its longitudinal dimension.

Figure 7:
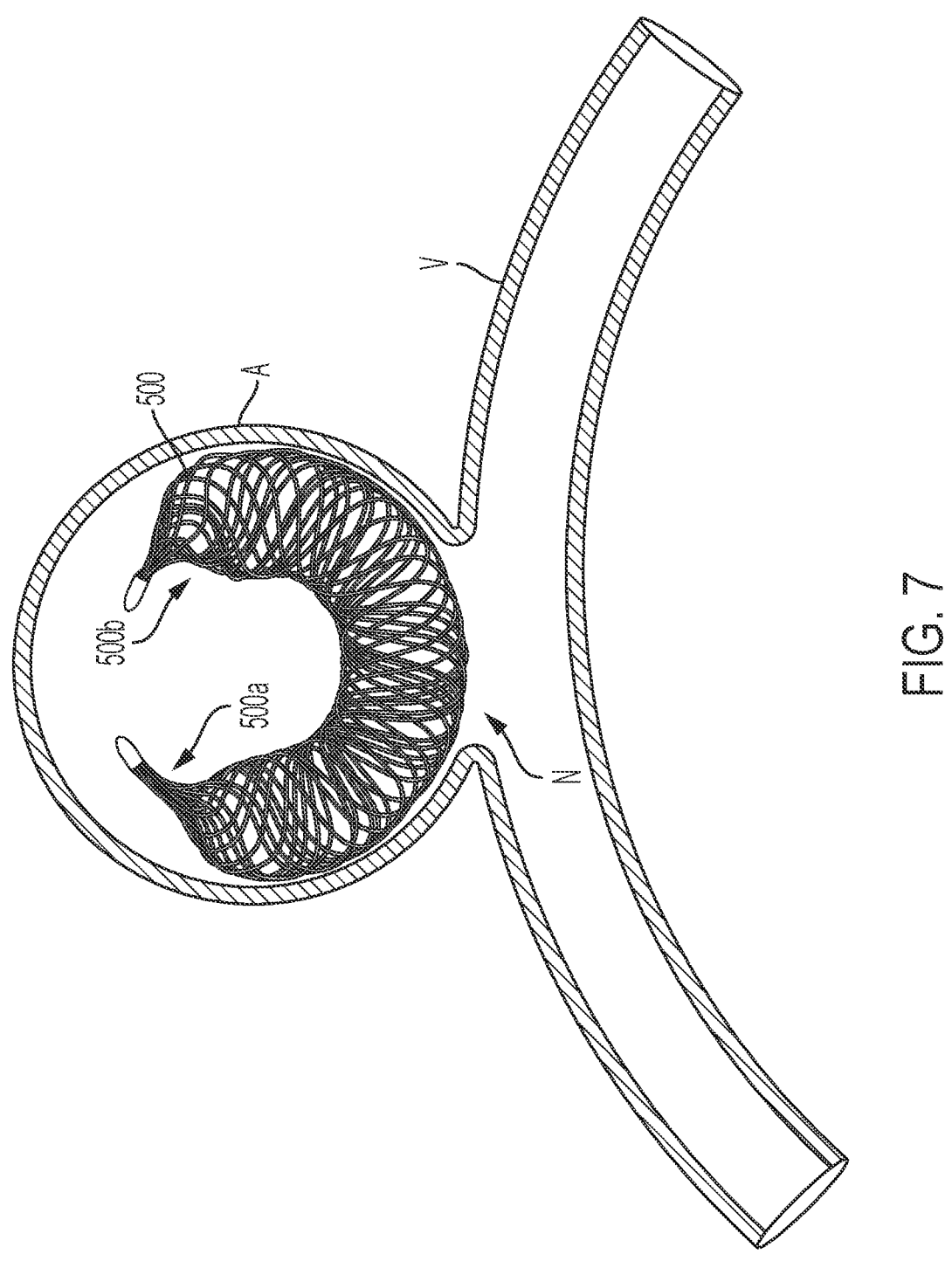
FIG. 7 shows the occlusive device of FIGS. 5 and 6 positioned within an aneurysm in accordance with several embodiments of the present technology.

FIG. 7 shows the device 500 positioned within an aneurysm. As shown, when the tubular structure is implanted within an aneurysm cavity in an expanded state, the tubular structure curves around a portion of the inner surface of the aneurysm such that the first and second closed end regions 500a, 500b are spaced apart from one another. When the device 500 is implanted, at least a portion of the tubular structure is positioned over the neck N of the aneurysm, thereby reducing blood flow entering the sac of the aneurysm and providing a scaffolding that promotes endothelialization across the covered portion of the neck, thus further reducing inflow.

According to some embodiments, the mesh 104 is a stent formed of a laser cut tube or a laser cut sheet that has been rolled into tubular form. In other embodiments, the mesh 104 is a tubular braid formed of a plurality of interwoven filaments. For example, the tubular structure may be formed of a plurality of wires, at least some of which (e.g., 25% of the wires, 50% of the wires, 80% of the wires, 100% of the wires, etc.) are made of one or more shape memory and/or superelastic materials. Some or all of the wires may have a diameter between about 0.0010 inches and about 0.0012 inches, about 0.0010 inches, about 0.0011 inches, 0.0012 inches (at least prior to etching). In some embodiments, some or all of the wires may be drawn-filled tubes ("DFT") having a radiopaque core (e.g., platinum) surrounded by a shape memory alloy and/or superelastic alloy (e.g., Nitinol, cobalt chromium, etc.).

All or a portion of the length of the tubular structure may have one or more coatings or surface treatments. For example, some or all of the tubular structure may have a lubricious coating or treatment that reduces the delivery force of the device 500 as the device 500 is advanced through the delivery catheter. In some embodiments, the coating may be relatively hydrophilic, such as a phosphorocholine compound. Additionally or alternatively, some or all of the tubular structure (or components thereof) may have a coating or treatment (the same as the lubricious coating, or a different coating) that enhances blood compatibility and reduces the thrombogenic surface activity of the braid (e.g., an antithrombogenic coating). In these and other embodiments, at least a portion of the tubular structure can be made of other suitable materials.

Figure 8:
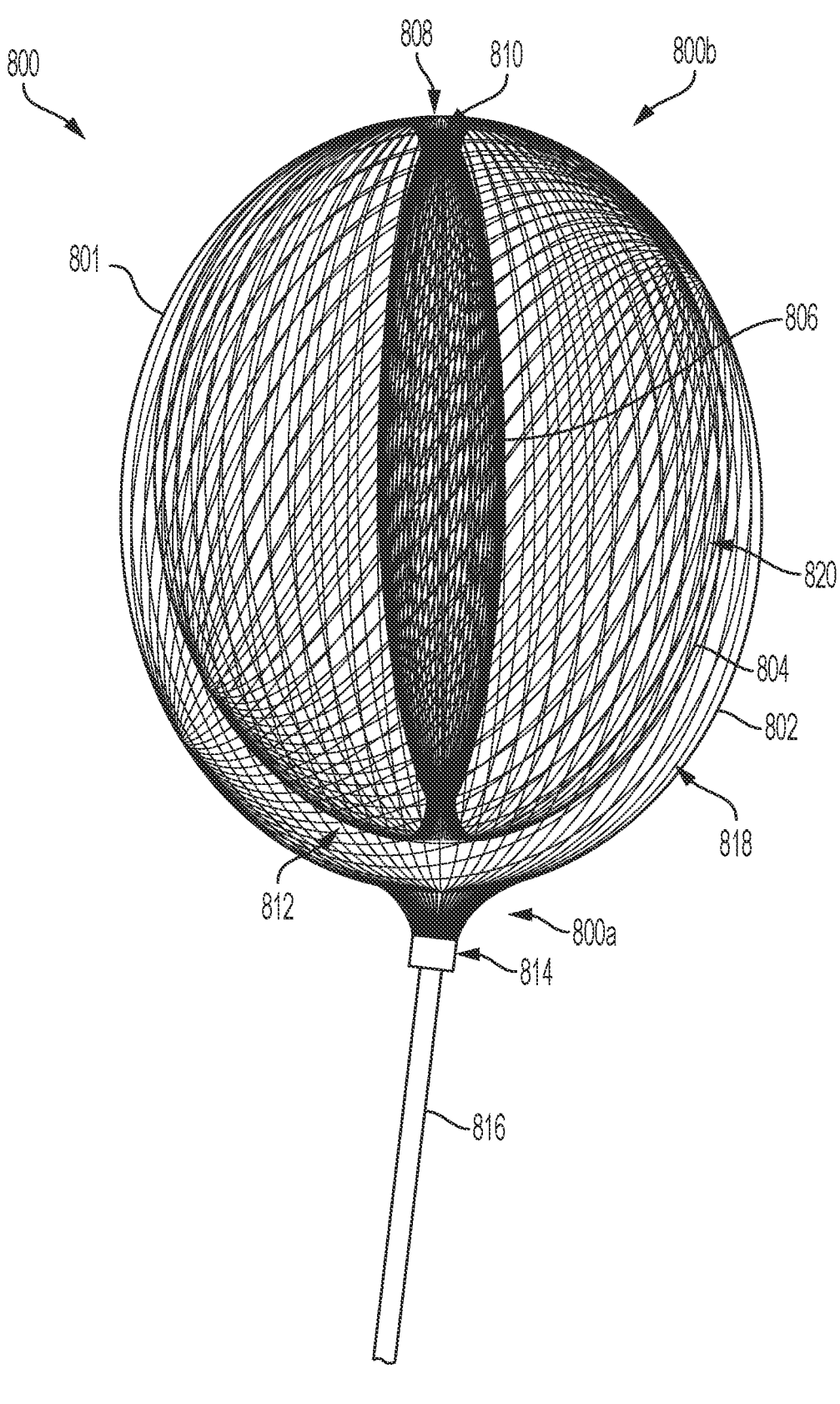
FIG. 8 is a side view of an occlusive device configured in accordance with several embodiments of the present technology.

FIG. 8 is a side view of an occlusive device 800 (or "device 800") configured in accordance with several embodiments of the present technology. In FIG. 8, a proximal end portion 800a of the occlusive device 800 is coupled to the distal end portion of a delivery member 816. The occlusive device 800 may comprise a self-expanding mesh 801 having a generally globular shape in an expanded, unconstrained state. The mesh 801 may comprise an outer layer 802 and an inner layer 804, each having a generally globular shape in the expanded state. In some embodiments, one or both of the outer layer and the inner layer may have other shapes. As shown in FIG. 8, the inner layer 804 may be disposed completely within an interior region defined by the outer layer 802. The outer layer 802 may be sized for implantation within an aneurysm cavity such that substantially all of the outer surface of the outer layer 802 is in contact with an inner surface of the aneurysm wall.

The device 800 may further comprise a column 806 extending between a proximal end portion and the distal end portion of the device 800. The column 806 may be disposed within the interior volume of both the inner layer 802 and the outer layer 804. The column 806 provides a support structure that adds considerable longitudinal strength to the device 800 that prevents or reduces the vertical compression of the mesh 801 during clinical use. Advantageously, the mesh 801 remains radially compliant so as to avoid aneurysm rupture. The column 806 also encourages thrombosis within the device 800.

In some embodiments, the mesh 801 may be formed of a plurality of wires, at least some of which (e.g., 25% of the wires, 50% of the wires, 80% of the wires, 100% of the wires, etc.) are made of one or more shape memory and/or superelastic materials. Some or all of the wires may have a diameter between about 0.0010 inches and about 0.0012 inches, about 0.0010 inches, about 0.0011 inches, 0.0012 inches (at least prior to etching). In some embodiments, some or all of the wires may be drawn-filled tubes ("DFT") having a radiopaque core (e.g., platinum) surrounded by a shape memory alloy and/or superelastic alloy (e.g., Nitinol, a cobalt chromium alloy, a cobalt nickel alloy, or any combination of the foregoing materials).

All or a portion of the length of some or all of the wires may have one or more coatings or surface treatments. For example, some or all of the wires may have a lubricious coating or treatment that reduces the delivery force of the device 800 as the device 800 is advanced through the delivery catheter to the aneurysm. The coating may be applied to only the outer layer 802, only the inner layer 804, or both. In some embodiments, the coating may be relatively hydrophilic, such as a phosphorocholine compound. Additionally or alternatively, some or all of the wires may have a coating or treatment (the same as the lubricious coating, or a different coating) that enhances blood compatibility and reduces the thrombogenic surface activity of the braid (e.g., an antithrombogenic coating). In these and other embodiments, at least a portion of the wires (or components thereof) can be made of other suitable materials.

In any of the foregoing embodiments, auxiliary fibrous materials may be optionally added to all or a portion of one, some, or all of the wires by weaving, tying, or other suitable permanent attachment methods.

CONCLUSION

Although many of the embodiments are described above with respect to systems, devices, and methods for treating a cerebral aneurysm, the technology is applicable to other applications and/or other approaches. For example, the occlusive devices, systems, and methods of the present technology can be used to treat any vascular defect and/or fill or partially fill any body cavity or lumen or walls thereof, such as to treat parent vessel occlusion, endovascular aneurysms outside of the brain, arterial-venous malformations, embolism, atrial and ventricular septal defects, patent ductus arteriosus, and patent foramen ovale. Additionally, several other embodiments of the technology can have different states, components, or procedures than those described herein. It will be appreciated that specific elements, substructures, advantages, uses, and/or other features of the embodiments described can be suitably interchanged, substituted or otherwise configured with one another in accordance with additional embodiments of the present technology. A person of ordinary skill in the art, therefore, will accordingly understand that the technology can have other embodiments with additional elements, or the technology can have other embodiments without several of the features shown and described above with reference to FIGS. 1A-8.

As used herein, the terms "generally," "substantially," "about," and similar terms are used as terms of approximation and not as terms of degree, and are intended to account for the inherent variations in measured or calculated values that would be recognized by those of ordinary skill in the art.

The descriptions of embodiments of the technology are not intended to be exhaustive or to limit the technology to the precise form disclosed above. Where the context permits, singular or plural terms may also include the plural or singular term, respectively. Although specific embodiments of, and examples for, the technology are described above for illustrative purposes, various equivalent modifications are possible within the scope of the technology, as those skilled in the relevant art will recognize. For example, while steps are presented in a given order, alternative embodiments may perform steps in a different order. The various embodiments described herein may also be combined to provide further embodiments.

Moreover, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Additionally, the term "comprising" is used throughout to mean including at least the recited feature(s) such that any greater number of the same feature and/or additional types of other features are not precluded. It will also be appreciated that specific embodiments have been described herein for purposes of illustration, but that various modifications may be made without deviating from the technology. Further, while advantages associated with certain embodiments of the technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein.

We claim:

1. A device for treating an aneurysm, the device comprising:

a mesh having a globular shape in an expanded configuration, wherein the mesh is configured to be implanted in an aneurysm in the expanded configuration, and wherein the mesh comprises:

a proximal end region, a distal end region, and a longitudinal axis extending therebetween, an outer shell, an inner shell having a proximal end region and a distal end region, the inner shell having a globular shape in an expanded configuration, wherein the inner shell is wholly contained by the outer shell, and a column extending along the longitudinal axis of the mesh between a proximal end region of the column and a distal end region of the column, wherein the column is disposed within the inner shell, wherein the proximal end region of the inner shell inverts into the proximal end region of the column such that the proximal end region of the column is continuous with the proximal end region of the inner shell, wherein the proximal end region of the column is disposed at the proximal end region of the device and the distal end region of the column is disposed at the distal end region of the device such that the column is configured to provide support along the longitudinal axis of the mesh, and wherein the column terminates distally at an opening at the distal end region of the inner shell.

2. The device of claim 1, wherein the distal end region of the mesh forms a curved surface that is concave towards an interior region of the mesh.

3. The device of claim 1, wherein the outer shell and the inner shell are continuous with one another at the distal end region of the mesh.

4. The device of claim 1, wherein the distal end region of the mesh forms a curved surface and the opening along the curved surface.

5. The device of claim 1, wherein the distal end region of the mesh does not include a hub.

6. The device of claim 1, wherein the column extends through an interior region of the inner shell.

7. The device of claim 1, wherein the outer shell is globular.

8. The device of claim 1, wherein the inner shell is globular.

9. The device of claim 1, wherein the mesh is a braid.

10. A device for treating an aneurysm, the device comprising:

a mesh having a globular shape in an expanded configuration, wherein the mesh is configured to be implanted in an aneurysm in the expanded configuration, and wherein the mesh comprises:

a proximal end region, a distal end region, and a longitudinal axis extending therebetween, an outer shell having a proximal end region and a distal end region, wherein the distal end region of the mesh terminates at the distal end region of the outer shell, and wherein the distal end region of the outer shell forms a curved surface that is concave towards an interior region of the mesh, an inner shell having a proximal end region and a distal end region, the inner shell having a globular shape in an expanded configuration, wherein the inner shell is wholly contained by the outer shell, and a column extending along the longitudinal axis of the mesh between a proximal end region of the column and a distal end region of the column, wherein the column is disposed within the inner shell, wherein the mesh inverts at the proximal end region of the column such that the proximal end region of the column merges with the proximal end region of the inner shell, wherein the proximal end region of the column is disposed at the proximal end region of the device and the distal end region of the column is disposed at the distal end region of the device such that the column is configured to provide support along the longitudinal axis of the mesh, and wherein the column terminates distally at an opening at the distal end region of the inner shell.

11. The device of claim 10, wherein the distal end region of the mesh forms a curved surface that is concave towards an interior region of the mesh.

12. The device of claim 10, wherein the outer shell and the inner shell are continuous with one another at the distal end region of the mesh.

13. The device of claim 10, wherein the distal end region of the mesh forms a curved surface and the opening along the curved surface.

14. The device of claim 10, wherein the distal end region of the mesh does not include a hub.

15. The device of claim 10, wherein the column extends through an interior region of the inner shell.

16. The device of claim 10, wherein the outer shell is globular.

17. The device of claim 10, wherein the inner shell is globular.

18. The device of claim 10, wherein the mesh is a braid.

* * * * *